US 6,730,109 B2

(12) United States Patent
Wöllmer

(10) Patent No.: US 6,730,109 B2
(45) Date of Patent: May 4, 2004

(54) MEDICAL GRIPPING INSTRUMENT AND METHOD FOR USING THIS MEDICAL GRIPPING INSTRUMENT

(75) Inventor: Wolfgang Wöllmer, Hamburg (DE)

(73) Assignee: Karl Storz GmbH & Co. KG (DE)

( * ) Notice: Subject to any disclaimer, the term of this patent is extended or adjusted under 35 U.S.C. 154(b) by 226 days.

(21) Appl. No.: 10/013,292

(22) Filed: Dec. 10, 2001

(65) Prior Publication Data

US 2002/0095178 A1 Jul. 18, 2002

Related U.S. Application Data

(63) Continuation of application No. PCT/EP00/05342, filed on Jun. 9, 2000.

(30) Foreign Application Priority Data

Jun. 11, 1999 (DE) ......................................... 199 26 555

(51) Int. Cl.$^7$ ............................................. A61B 17/00
(52) U.S. Cl. ..................................................... 606/207
(58) Field of Search ................................ 606/205–209, 606/210, 139, 144

(56) References Cited

U.S. PATENT DOCUMENTS

| 5,147,373 A | 9/1992 | Ferzli ........................ 606/144 |
| 5,201,759 A | 4/1993 | Ferzli ........................ 606/207 |
| 5,261,917 A | * 11/1993 | Hasson et al. .............. 606/206 |
| 5,318,013 A | 6/1994 | Wilk ........................... 128/20 |
| 5,441,494 A | 8/1995 | Ortiz ............................ 606/1 |
| 5,456,695 A | 10/1995 | Herve Dallemagne ...... 606/207 |
| 5,549,636 A | * 8/1996 | Li ................................. 606/206 |
| 5,895,353 A | 4/1999 | Lunsford et al. ............. 600/209 |

FOREIGN PATENT DOCUMENTS

| DE | 33 37 016 | 12/1984 |
| DE | 41 00 235 | 8/1992 |
| DE | 44 18 449 | 5/1995 |
| DE | 44 00 409 | 7/1995 |
| WO | WO 99/05974 | 2/1999 |

* cited by examiner

Primary Examiner—Kevin T. Truong
(74) Attorney, Agent, or Firm—St. Onge Steward Johnston & Reens LLC

(57) ABSTRACT

The invention relates to a medical gripping instrument, especially for use in microlaryngoscopy, comprising a longitudinal shaft on whose distal end a pincer part is arranged, which can be moved between a closed and an opened position. A handle consisting of a fixed handle part and of a handle part that can pivot in relation to the fixed handle part is arranged on the proximal end of said shaft. The pincer part is moved via a push/pull rod, which is mounted in the shaft and which is connected to a pivotal handle part. The gripping instrument also comprises a spreading part, which can be tilted from the shaft. The aim of the invention is to create a gripping instrument of the aforementioned embodiment, which is not only simple in its structure and easy to be manipulated, but also ensures a protection of the tissue to be preserved. The said medical gripping instrument is characterized in that the spreading part, which can be pivoted from the shaft, is arranged on the distal end of said shaft next to the pincer part; and that it can be tilted within a certain range into an approximate right-angled position to the range of adjustment of the pincer part.

10 Claims, 3 Drawing Sheets

MEDICAL GRIPPING INSTRUMENT AND METHOD FOR USING THIS MEDICAL GRIPPING INSTRUMENT

This application is a continuation of pending International Application PCT/EP00/05342 filed on Jun. 9, 2000, which designates the United States and claims priority from German Application 199 26 555.0 filed on Jun. 11, 1999.

FIELD OF THE INVENTION

The invention relates to a medical gripping instrument, especially for use in microlaryngoscopy, comprising a longitudinal shaft on whose distal end a pincer part is arranged, which can be moved between a closed and an opened position. A handle consisting of a fixed handle part and of a handle part that can pivot in relation to the fixed handle part is arranged on the proximal end of said shaft. The pincer part is moved via a push/pull rod, which is mounted in the shaft and which is connected to a pivotal handle part. The gripping instrument also comprises a spreading part, which can be tilted from the shaft. In addition, the invention relates to a process for using this medical gripping instrument in microsurgical and especially in laser-surgical microlaryngoscopy.

BACKGROUND OF THE INVENTION

It is common in microsurgical and especially in laser-surgical microlaryngoscopy, in which tissues are to be removed, to insert a gripping instrument into the patient's body through the shaft of a fixed endoscope. On the one hand, this procedure facilitates the severing of a tissue part by means of another medical instrument, such as a laser, and, on the other hand, serves to remove the severed tissue from the patient's body. The particular risk in laser-surgery is that the tissue to be spared will also be damaged during such a surgery, especially due to the heat caused by the use of laser.

For example, a medical gripping instrument of the aforementioned type has been disclosed in U.S. Pat. No. 5,456, 695 A. The gripping instrument disclosed therein comprises a handle consisting of two handle parts. A pincer part on the distal end of the shaft can be moved between a closed and an opened position by means of said handle. In addition to said pincer part on the distal end of the shaft, a fan-shaped spreading part is arranged on the center part of said shaft, over which the individual fan blades used as retractors within the pincer part's range of adjustment can be pivoted from the shaft so as to press the tissue to the side, for example. The spreading part can be pivoted from its resting position in the shaft into the tilted spread position by turning the ring. The said ring is arranged on the distal end of the handle, that is, within the shaft's range of extension.

Apart from the fact that it is necessary to always use both hands for operating with the aforementioned gripping instrument if both the pincer part and the spreading part must be used at the same time, since it is not possible to use the handle parts and simultaneously turn the ring with a single hand only, the drawback of the aforementioned gripping instrument is that there is a distance between the spreading part and the pincer part when said spreading part has been shifted towards the proximal end of the shaft, and that said spreading part is used within the pincer part's range of adjustment. Especially in a restricted space, as in laryngoscopy for example, this design of the spreading part makes it difficult to protect the non-operable tissue so that only grip the tissue held by the pincer part is exposed to surgical intervention.

In accordance with the current state of technology, it is the objective of the present invention to provide a gripping instrument of the type mentioned at the beginning, which is simple in its structure, easy to be used, which ensures that the tissue to be removed will be protected. Moreover, it is the objective of the present invention to provide a procedure for the use of said medical gripping instrument.

The solution to this objective is characterized in that the spreading part, which can be tilted from the shaft, is—in addition to the pincer part—arranged on the distal end of the shaft, and that said spreading part can be tilted from the shaft within a certain range into an approximate right-angled position to the range of adjustment.

In the present invention, through the arrangement of the spreading part on the distal end of the shaft, i.e. in immediate proximity to the pincer part, the tissue to be preserved, which is immediately adjacent to the tissue to be removed and gripped by the pincer part, can be pushed aside, even in restricted areas of operation, so that the said tissue to be preserved will not be affected. Furthermore, the spreading part's approximately right-tangled tilting to the range of adjustment of the pincer part allows a largely independent movement both of the spreading part and of the pincer part.

The manipulation of the gripping instrument according to the present invention, and especially the surgery carried out with a single hand, is made possible because the spreading part can be tilted by means of an additional handle part of the handle.

The use of the said gripping instrument equipped with the additional spreading part makes it possible to keep the tissue to be preserved separate from the area of surgery, in order to provide more space and a better overview for surgery. Moreover, the advantage of the gripping instrument according to the present invention is that it can be used directly by manipulating the said gripping instrument, and thus that this additional accessory will be available to the surgeon at any time.

The gripping instrument in accordance with the present invention allows a facility in its use in that the pivotal handle part can be fixed in its respective position to the fixed handle part for adjusting the pincer part. By locking the pincer part in the gripping position, the surgeon now has the possibility of using the spreading part without having to move the pincer part at all.

According to a preferred embodiment of the present invention, a locking arm arranged on one of the two handle parts is used for fixing the pincer part, whereas the said locking arm is interacting with a locking element attached on the other handle part. As an advantageous feature, the said locking arm is provided with a saw-toothed profile on its surface.

According to a practical and preferred embodiment of the present invention, it is suggested that the locking arm is pivotal on one of the handle parts and, moreover, that it is spring-loaded in direction towards the stop location.

The invention's gripping instrument can be especially well manipulated if the pincer part and the spreading part can be moved into an opened position, that is, tilted from the shaft, by as much as 90°; preferably 50°.

SUMMARY OF THE INVENTION

The procedure in accordance with the present invention for using said gripping instrument in microsurgical, and especially in laser-surgical microlaryngoscopy, is characterized in the following steps:

a) inserting the medical gripping instrument through a shaft of a fixed endoscope;

b) opening the pincer part over both accompanying handle parts of the handle, and gripping the tissue to be removed;

c) tilting the spreading part over the additional handle part of the handle;

d) keeping the tissue parts separate from the area of surgery by means of the spreading part, in order to provide more space and a better view, especially in laser surgery;

e) severing the tissue gripped by the pincer part by means of a surgical instrument, especially by means of laser; and f) moving back the spreading part onto the shaft after the surgery, and withdrawing the medical gripping instrument together with the tissue to be removed.

Thus, the procedure according to the present invention enables the surgeon, by means of the spreading part, to selectively separate from the area of surgery the tissue to be preserved.

Finally, the procedure according to the present invention can be simplified if the handle parts of the pincer part can be fixed in gripping position prior to tilting the spreading part.

BRIEF DESCRIPTION OF THE DRAWINGS

The following description of the attached drawing defines the features and advantages, which are explained by means of an example of the preferred embodiment of a medical gripping device according to the present invention. The illustrations are as follows:

FIG. 1b An overhead view of the depiction shown in FIG. 1a.

FIG. 2b An overhead view of the depiction shown in FIG. 2a.

DETAILED DESCRIPTION OF THE INVENTION

Figure 1A:
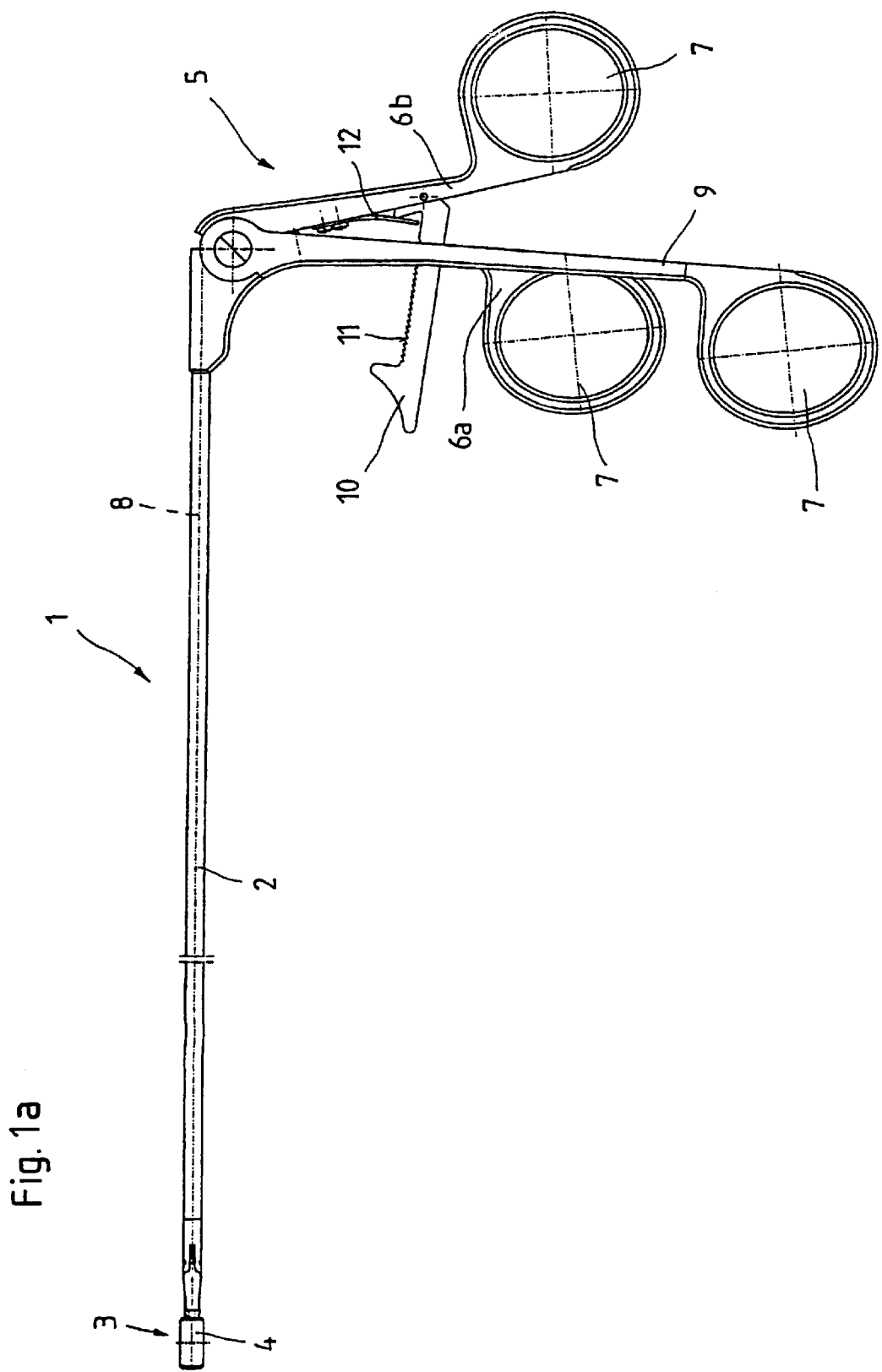
FIG. 1a A lateral view of a medical gripping instrument according to the present invention, wherein the pincer part is in a closed position and the spreading part is not tilted.
Figure 1B:
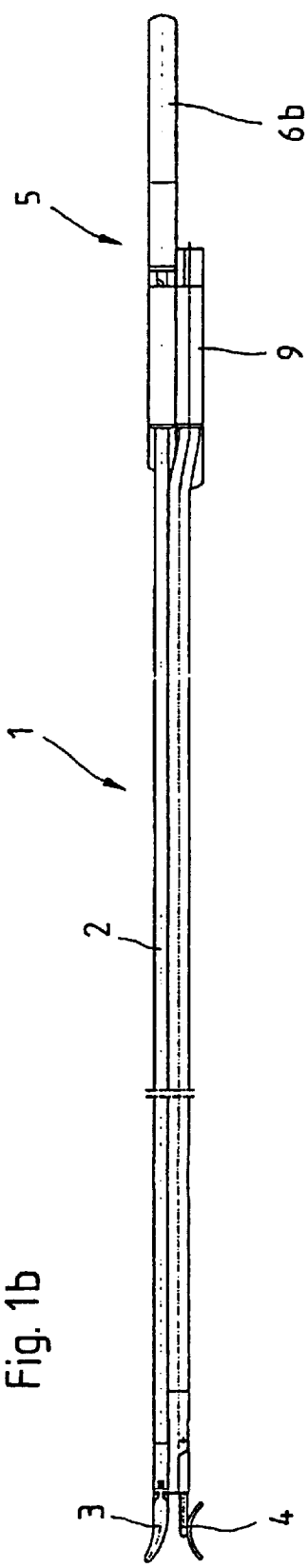
Figure 2B:
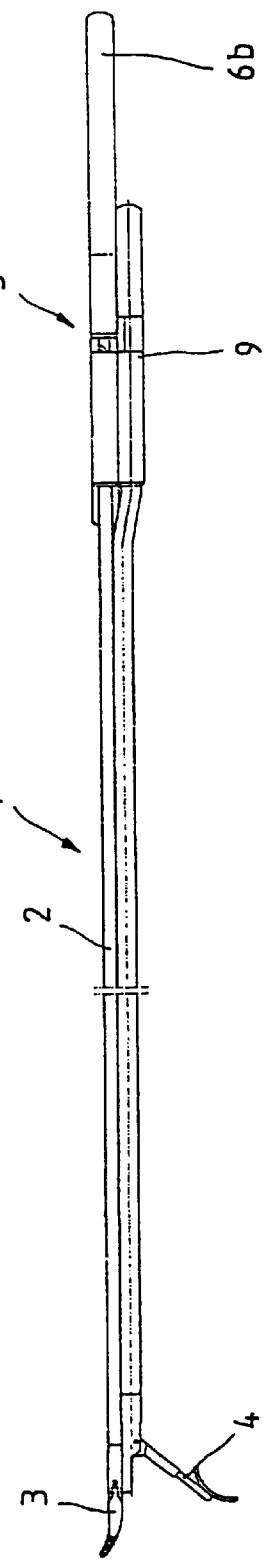

FIG. 1a shows a medical gripping instrument designed as gripping pincer 1, which is especially suitable for the use in microlaryngoscopy. As shown especially in FIG. 1b and FIG. 2b, the said gripping pincer 1 comprises a longitudinal shaft 2 on whose distal end a pincer part 3 as well as a spreading part 4, which can pivot in relation to the shaft 2 of the gripping pincer 1, are arranged.

A handle 5 is arranged on the proximal end of the shaft 2, and the pincer part 3 as well as the spreading part 4 can be manipulated by means of said handle 5. The manipulation of the pincer part 3 is carried out by means of the fixed handle part 6a as well as the pivotal handle part 6b, which can be tilted in relation to said fixed handle part 6a. The said fixed handle part and the pivotal handle part 6b are respectively provided with lugs 7 to control said handle parts 6a and 6b. The pincer part 3 is moved between the closed position shown in FIGS. 1a and 1b and the opened position shown in FIGS. 2a and 2b by means of a push/pull rod 8, which is mounted in the shaft 2 of the gripping pincer 1. Moreover, one end of said push/pull rod 8 is connected to the pincer part 3, while the other end is connected to the pivotal handle part 6b.

As shown by the example of a preferred embodiment according to the present invention, an additional handle part 9 arranged on the handle 5 is used for moving the spreading part 4, which is arranged on the distal end of the gripping pincer 1 as well. The example of the preferred embodiment of a medical gripping instrument shows that the said handle part 9—also provided with a lug 7—of the spreading part 4 has a greater length than the handle parts 6a and 6b used for manipulating the pincer part 3. However, the length of the individual handle parts 6a, 6b and 9 does not affect the functionality of a medical gripping instrument designed in this fashion.

Figure 2A:
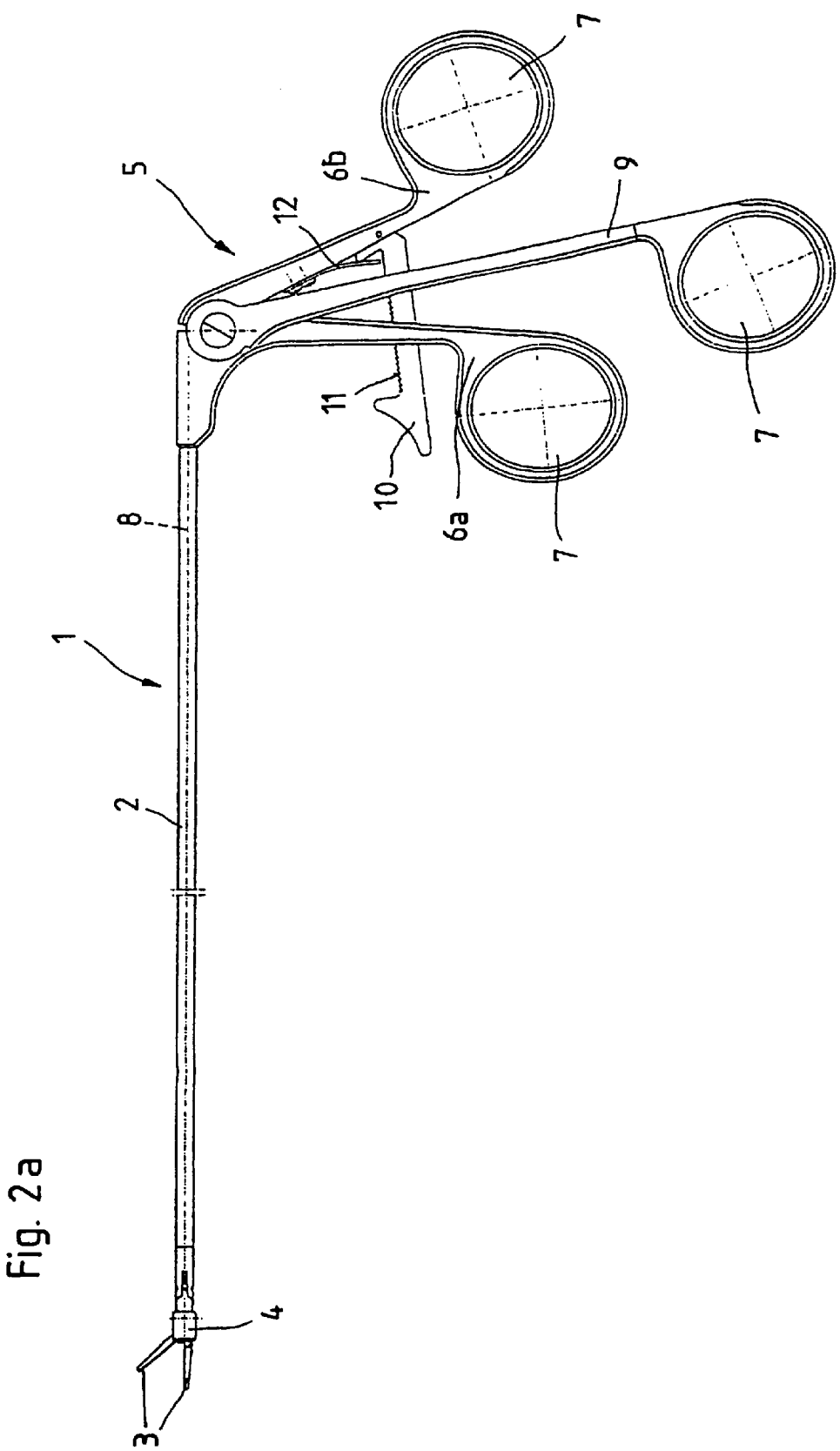
FIG. 2a A lateral view of the medical gripping device shown in FIG. 1a, wherein the pincer part is in an opened position and the spreading part is tilted.

As is shown in FIG. 1a and FIG. 2a, a locking arm 10 is arranged on the pivotal handle part 6b, which is used for manipulating the pincer part 3. The top side of said locking arm 10 is provided with a saw-tooth profiling 11, which is interacting with a locking element (not shown) arranged on the fixed handle part 6a in a way that the handle parts 6a, 6b can be fixed for moving the pincer part 3, and thus that the pincer part 3 itself can be fixed in its respective position.

The gripping instrument according to the present invention works as described below.

FIG. 1a shows the position in which the gripping pincer 1 is being inserted through the shaft of an endoscope (not shown) into the patient's body. Subsequently, the handle parts 6a and 6b are used for opening the pincer part 3 and the pincer part 3 grips the tissue to be removed. The pivotal handle part 6b can then be fixed in the position pivoted in relation to the fixed handle part 6a. The said pivotal handle part 6b will be fixed by means of the locking arm 10 provided with the saw-tooth profiling 11 as well as by the interaction of the locking element with said saw-tooth profiling 11, wherein said locking element is arranged on the fixed handle part 6a. At this point and without any further manipulation to be carried out by the surgeon, the pincer part 3 is now firmly gripping the tissue to be removed.

In order to provide sufficient space and an unobstructed view in surgery, the surgeon now is able to tilt the spreading part 4 from the shaft 2 of the gripping pincer 1 by means of the pivotal handle part 9 and to keep the tissue to be preserved separate from the area of surgery. The use of the spreading part 4 is especially advantageous in laser-surgery, since the tissue to be preserved can be protected from the thermal impact caused by laser.

The tissue to be removed will be stressed under tension due to the gripping pincer 1 during surgery in order to ensure quick and accurate removal of said tissue.

After surgery, the spreading part 4 will be moved back on the shaft 2 of the gripping pincer 1 and said gripping pincer 1 will be withdrawn from the patient's body together with the tissue gripped by the pincer part 3.

The handle parts 6a, 6b will be released from the engaged position by pushing down the locking arm 10 arranged pivotally on the handle part 6b, wherein said locking arm 10 is pushed down against the force created by a spring 12 holding the said locking arm 10 in a locked position. The said locking arm 10 is pushed down until the locking element will be disengaged from the saw-tooth profiling 11 on said locking arm 10.

In view of the design of the medical gripping instrument described herein, the surgeon will be enabled for the first time to selectively keep the tissue to be preserved separate from the area of surgery during microlaryngoscopy by using only one single instrument.

Illustration Key 1 gripping pincer
2 shaft
3 pincer part 4 spreading part
5 handle
6a fixed handle part 12 spring
6b pivotal handle part
7 lug
8 push/pull rod
9 additional handle part
10 locking arm
11 saw-tooth profiling
12 spring

What is claimed is:

1. A medical gripping instrument especially designed for use in microlaryngoscopy, comprising a longitudinal shaft on whose distal end a pincer part is arranged, which can be moved between a closed and an opened position, and a handle consisting of a fixed handle part and of a handle part that can pivot in relation to the fixed handle part is arranged on the proximal end of said shaft, wherein the pincer part is moved via a push/pull rod, which is mounted in the shaft and which is connected to the pivotal handle part; as well as a spreading part, which can be tilted from the shaft, characterized in that the spreading part to be tilted from the shaft is, in addition to the pincer part, arranged on the distal end of said shaft and located directly close to said pincer part and can be tilted from the shaft within a plane approximate in right-angled position to the plane of adjustment of the pincer part.

2. A medical gripping instrument in accordance with claim 1, characterized in that the spreading part can be moved by means of an additional pivotal handle part.

3. A medical gripping instrument in accordance with claim 1, characterized in that the pivotal handle part can be fixed in its respective position in relation to the fixed handle part for moving the pincer part.

4. A medical gripping instrument in accordance with claim 3, characterized in that the locking arm is arranged on one of the handle parts so as to fix the said handle parts used for moving the pincer part, wherein the said locking arm is interacting with a locking element arranged on the other handle part.

5. A medical gripping instrument in accordance with claim 4, characterized in that the locking arm is provided with a saw-tooth profiling on its surface.

6. A medical gripping instrument in accordance with claim 4, characterized in that the locking arm is arranged pivotally on one of the handle parts and that it is spring-loaded in direction towards the stop location.

7. A medical gripping instrument in accordance with claim 1, characterized in that the pincer part can be moved into an opened position by up to 90°.

8. A medical gripping instrument in accordance with claim 1, characterized in that the spreading part can be tilted by up to 90° from the shaft.

9. A procedure for the use of a medical gripping instrument, especially in accordance with claim 1, in microsurgical, and especially in laser-surgical microlaryngoscopy, characterized through the following procedures:
inserting the said medical gripping instrument through the shaft of a fixed endoscope;
moving the pincer part in an opened position by means of both accompanying handle parts of the handle, and gripping the tissue to be removed;
tilting the spreading part by means of the additional handle part arranged on the handle;
keeping the tissue to be preserved separate from the area of surgery by means of the spreading part so as to provide more space and a better view, especially for laser surgery;
severing the tissue gripped by the pincer part by a surgical instrument, especially by means of laser, and
moving back the spreading part onto the shaft after surgery, and withdrawing the medical gripping instrument together with the tissue to be removed.

10. The procedure in accordance with claim 9, characterized in the following procedure:
fixing the handle parts of the pincer part in gripping position prior to tilting the spreading part.

* * * * *